(12) United States Patent
Guitard et al.

(10) Patent No.: US 9,491,962 B2
(45) Date of Patent: Nov. 15, 2016

(54) USE OF CHICORIC ACID AND DERIVATIVES FOR REGULATING SKIN PIGMENTATION

(75) Inventors: Marjorie Guitard, Savigny (CH); Rachid Bel Rhlid, Savigny (CH); Angus Moodycliffe, Savigny (CH); Fabiola Dionisi, Epalinges (CH)

(73) Assignees: Nestec S.A., Vevey (CH); L'Oreal, Paris (FR)

( * ) Notice: Subject to any disclaimer, the term of this patent is extended or adjusted under 35 U.S.C. 154(b) by 13 days.

(21) Appl. No.: 13/805,872

(22) PCT Filed: Jun. 28, 2011

(86) PCT No.: PCT/EP2011/060765
§ 371 (c)(1),
(2), (4) Date: Dec. 20, 2012

(87) PCT Pub. No.: WO2012/000960
PCT Pub. Date: Jan. 5, 2012

(65) Prior Publication Data
US 2013/0095070 A1    Apr. 18, 2013

(30) Foreign Application Priority Data
Jun. 30, 2010  (EP) ..................................... 10167866

(51) Int. Cl.
| | |
|---|---|
| A01N 65/00 | (2009.01) |
| A23L 1/30 | (2006.01) |
| A61K 8/365 | (2006.01) |
| A61K 8/97 | (2006.01) |
| A61K 8/99 | (2006.01) |
| A61K 31/216 | (2006.01) |
| A61K 36/28 | (2006.01) |
| A61Q 19/00 | (2006.01) |
| A61Q 19/02 | (2006.01) |
| A61K 8/37 | (2006.01) |

(52) U.S. Cl.
CPC ............ *A23L 1/3002* (2013.01); *A23L 33/105* (2016.08); *A23L 33/135* (2016.08); *A61K 8/365* (2013.01); *A61K 8/37* (2013.01); *A61K 8/97* (2013.01); *A61K 8/99* (2013.01); *A61K 31/216* (2013.01); *A61K 36/28* (2013.01); *A61Q 19/00* (2013.01); *A61Q 19/02* (2013.01); *A61K 2800/884* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 4,671,962 A  * | 6/1987 | Leroux ........................... | 426/51 |
| 5,164,185 A | 11/1992 | Charpin et al. | |
| 6,379,716 B2 * | 4/2002 | Santhanam et al. .......... | 424/737 |
| 7,226,623 B2 * | 6/2007 | Ripoll et al. .................. | 424/725 |
| 7,431,939 B1 * | 10/2008 | Buddington et al. ......... | 424/439 |
| 8,404,746 B2 * | 3/2013 | Andary et al. ................ | 514/557 |
| 2004/0170581 A1 | 9/2004 | Henry et al. | |
| 2007/0183996 A1 | 8/2007 | Okombi et al. | |

FOREIGN PATENT DOCUMENTS

| | | |
|---|---|---|
| EP | 1570839 | 9/2005 |
| EP | 2210504 | 7/2010 |
| HU | 57604 | * 12/1991 |
| JP | 406219958 | * 8/1994 |
| JP | 2005194246 | 7/2005 |
| WO | 0166076 | 9/2001 |

OTHER PUBLICATIONS

Publicaiton "Phenol-Explore: Showing report on Vegetables" dated/posted Jan. 2010; p. 1-8 from webpage http://phenol-explore.eu/40 retrieved on Jun. 11, 2015.*

* cited by examiner

*Primary Examiner* — Vera Afremova
(74) *Attorney, Agent, or Firm* — K&L Gates LLP

(57) ABSTRACT

The present invention relates generally to the field of food supplements for cosmetic purpose. More specifically, the present invention aims to provide an ingredient containing chicoric acid and/or derivatives for preventing and/or treating hyper-pigmentation of skin, skin color imperfections such as age-spots and other skin disorders characterized by abnormal pigments. The present invention also aims at improving skin tone as well as providing a skin lightening agent.

20 Claims, 2 Drawing Sheets

USE OF CHICORIC ACID AND DERIVATIVES FOR REGULATING SKIN PIGMENTATION

CROSS REFERENCE TO RELATED APPLICATIONS

Figure 1:
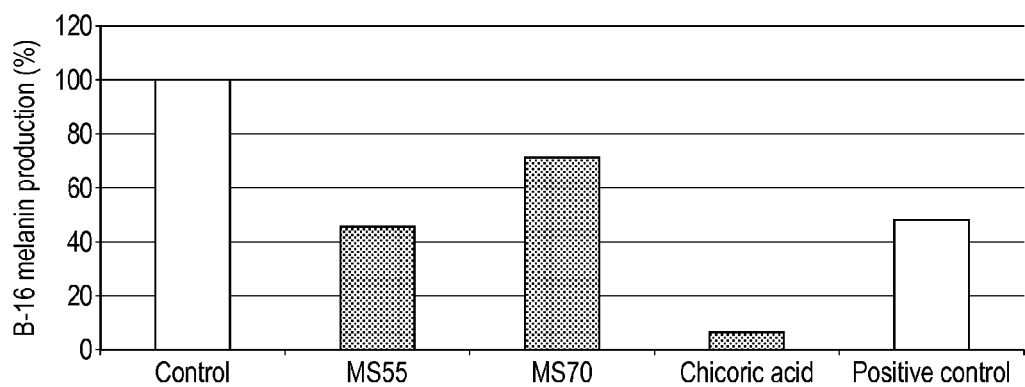

The present application is a National Stage of International Application No. PCT/EP2011/060765, filed on Jun. 28, 2011, which claims priority to European Patent Application No. 10167866.2, filed Jun. 30, 2010, the entire contents of which are being incorporated herein by reference.

The present invention relates generally to the field of food supplements for cosmetic purpose. More specifically, the present invention aims to provide an ingredient containing chicoric acid and/or derivatives for preventing and/or treating hyper-pigmentation of skin, skin color imperfections such as age-spots and other skin disorders characterized by abnormal pigments. The present invention also aims at improving skin tone as well as providing a skin lightening or whitening agent.

BACKGROUND OF THE INVENTION

Skin color is primarily determined by the amount and type of melanin, a brown pigment present in the skin. Lower amounts of melanin result in lighter skin color while higher amounts result in darker skin color. Also, hyper-pigmentation in the skin is caused by the over expression or accumulation of melanin in the skin. As a result, the pathway involved in melanin production has been the target for many inhibitors so as to reduce the levels produced. One of the principal enzymes involved in the melanin pathway is tyrosinase.

The synthesis of melanin is a process under hormonal control, including the melanocyte stimulating hormone (MSH) and adrenocorticotropic hormone (ACTH) peptides that are produced from the precursor proopiomelanocortin. It is stimulated by the DNA damages that are caused by UVB-radiations as well.

Then, exposure to the sun over time can induce many biochemical reactions in the skin, leading to sunburn and tanning, for example. Other consequences of exposure to the sun accumulate over time. These changes can result in the development of age spots and create an uneven, mottled skin tone. Unfortunately, many of the commercially available products in today's market are either only marginally effective, or contain active agents that are unstable and lose their potency when incorporated into a final formula.

The ability to modify the expression of pigment content in the skin, to promote an evenness skin tone or lightening skin tone, is highly desired in today's society. Many people desire to modify their skin tone, to reduce aging spots, etc., or for purely cosmetic reasons.

As a result, efforts to develop effective compositions have focused on agents that inhibit the activity of tyrosinase. For example, a variety of tyrosinase inhibitors, such as hydroquinone, vitamin C, cystein, kojic acid, arbutin and glutathione among others have been proposed in topical compositions. Also, a variety of dermatological compositions have been suggested for improving the appearance of pigment disorders such as that observed in melasma, freckles, vitiligo, piebaldism, phenylketonuria, and the like, and/or for cosmetic purposes.

Also, the use of skin bleaching compositions is widely expanded. However, they either destroy melanin or inhibit its formation. Many of these contain harsh chemicals such as peroxides, acids or formaldehyde, or thiolated materials. Less stringent therapies have other disadvantages.

Topical retinoid and topical corticosteroids have been suggested as hypo-pigmenting agents, as have laser treatment and chemical peels, but these fall short of desirable responses.

Other compositions suggested the use on the skin of natural materials, which have in some cases been used for centuries in Asia or Europe to bleach skin and skin areas, or enhance the appearance of fair skin. These include the use of lemon, orange, cucumber, ginkgo, carob, rose fruit, geranium herb, cinnamon, sweet marjoram, rosemary, etc. . . . . .

In order to combat disorders related to abnormal pigment or to lighten skin tone, various compounds which, when applied topically to the skin, are capable of reducing tyrosinase activity and consequently limiting melanin production, have thus been proposed. Unfortunately, the treatments currently available are not entirely satisfactory, in particular in terms of the side effects which are frequently associated therewith, such as irritant side effects with certain topical agents.

It would thus be highly desirable to have alternative preparations that do not have the drawbacks of those described in the prior art. In particular, it would be highly desirable to develop nutritional cosmetic compositions to be administered via oral route that have improved stability and efficacy to promote an evenness skin tone or to lighten skin tone.

There also remains a need to active agents that are effective for treating and/or preventing skin pigmentation disorders, in particular those due to environmental factors or aging.

The object of the present invention is to meet these needs.

SUMMARY OF THE INVENTION

The present inventors could achieve this object by providing a food supplement composition that comprises at least an ingredient containing chicoric acid and/or derivatives.

Thus, according to a first subject, the invention relates to the cosmetic use of an effective amount of at least an ingredient containing chicoric acid and/or derivatives as an active agent for treating and/or preventing skin pigmentation disorders. Such skin disorder are in particular those due to age or to environmental factors (e.g. UV), such as age-spots. It may also be skin disorders that are observed in melasma, freckles, vitiligo, piebaldism, phenylketonuria, and the like.

The present inventors have discovered that chicoric acid and derivatives effectively suppress the formation of melanin, melanogenesis, despite the fact that the extracts show little to no inhibition of tyrosinase activity. This result is surprising and unexpected considering the pivotal role of tyrosinase in melanogenesis and the focus of development efforts in the art to inhibit this enzyme.

For the purpose of the present invention, the term "skin" is intended to mean the skin of the face or of the body.

For the purpose of the present invention the term "effective amount", is intended to mean an amount sufficient to obtain the expected effect.

For the purpose of the present invention the term "prevent" is intended to mean the fact of reducing the risk of occurrence of the manifestation of the disorder under consideration.

The present invention is also directed towards the cosmetic use of the above-mentioned ingredient, as an active agent for treating and/or preventing the skin pigment imperfections. As a result, the complexion becomes brighter and more homogeneous, without areas of dyschromia, or of dryness.

The present invention is also directed towards the cosmetic use of an effective amount of at least an ingredient containing chicoric acid and/or derivatives according to the invention, as an active agent for whitening or lightening skin tone.

The present inventors have also discovered that the ingredient according to the invention further improves hydration and/or skin barrier function.

A use in accordance with the present invention may also comprises the use of at least an ingredient containing chicoric acid and/or derivatives, in combination with an effective amount of at least one active agent for further improving skin hydration or skin ageing, in particular as described hereinafter.

According to another of its aspects, the subject of the invention is a method, in particular a cosmetic method, for treating and/or preventing skin tone imperfections and the disorders associated with hyper-pigmentation, in particular aesthetic disorders, in an individual, comprising at least one step of administering, to said individual, at least an ingredient containing chicoric acid and/or derivatives according to the invention.

Compositions according to the present invention are orally administrable. This has the advantage of acting globally on the entire skin, in its deep layers (dermis, hypodermis), by means of a rapid and relatively non-restrictive mode of administration. Specifically, the metabolites and other active nutriments are in particular distributed within the dermal matrix by means of the bloodstream. Oral administration also has the advantage of a rapid and relatively non-restrictive mode of administration.

DETAILED DESCRIPTION OF THE INVENTION

Ingredient Containing Chicoric Acid and or Derivatives
Chicoric acid is

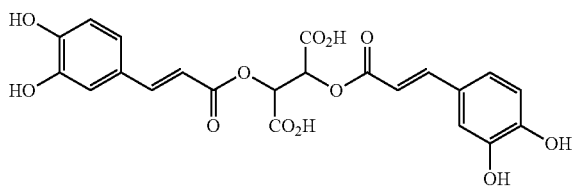 [SMILES: O=C(/C=C/c1ccc(O)c(O)c1)OC(C(=O)O)C(OC(=O)/C=C/c1ccc(O)c(O)c1)C(=O)O]

and derivatives of chicoric acid include

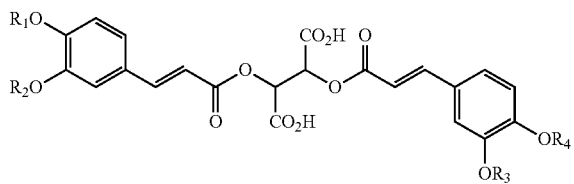

$R_1$, $R_2$, $R_3$ and/or $R_4$ may be identical or may differ from one another.

In one embodiment, $R_1$, $R_2$, $R_3$ and/or $R_4$ may be selected from the group consisting of H; $CH_3$; $C_1$-$C_3$-alkyl; aryl, such as phenyl, benzyl, tolyl, o-xylylalkyl; $C_1$-$C_3$-acyl; amino acids; mono-, di- or oligosaccharides. Oligosaccharides contain between two and nine monosaccharide units. $R_1$, $R_2$, $R_3$ and $R_4$ may be identical and/or may differ from one another.

One typical derivative of chicoric acid is for example the following compound:

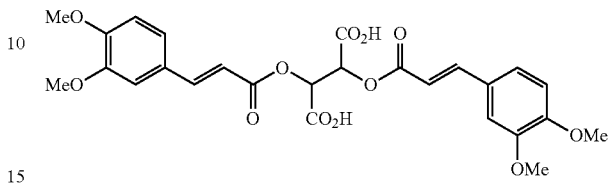

The ingredient containing chicoric acid and/or derivatives thereof may be any ingredient that contains chicoric acid and/or derivatives thereof, either naturally or in added form, but is preferably a natural foodstuff such as lettuce, chicory, dandelion, grape, grape pomace; or combinations or extracts thereof.

In a preferred embodiment, the plant material is in the form of chicory or an extract thereof. The chicory extract can be made from any suitable part of the plant material includes, for example, the root, the pulp, the like or combinations thereof.

Suitable extracts of chicory for the purpose of the present invention are also extracts that are commercially available, such as for example Leroux MS55 (commercially available from Leroux SAS, France)

In a particular preferred embodiment of the present invention, suitable extracts of chicory may be prepared by any means that are known in the art, e.g., by steam extraction, solvent extraction, distillation, pressing or grinding.

For ease of handling, the plant material is preferably in a dried and comminuted or powder form. As described below, the processes utilize dried, comminuted chicory and/or extracts thereof. However, it is to be understood that any suitable plant material may be used in any suitable form and added to the product according to the present invention.

The extract is processed such that its flavor can be enhanced. For example, bitter flavors which are typically associated with plant materials, such as chicory, can be removed by processing the plant into an extract. The extract can also be prepared such that the amount of bioactive agent in the final extract product can be desirably controlled.

It should be appreciated that the plant material can be processed to form an extract in a variety of different and suitable ways. In general, the plant material, such as the chicory root, is ground, powdered or provided in any suitable form. The plant material can then be further processed in a number of different stages to produce the product extract. In an embodiment, a defatting procedure is performed on the plant material to produce an extract that results from fats removed from the plant material. The defatting procedure can be conducted under any suitable defatting process conditions with any suitable types and amounts of solvents including, for example, hexane.

In an embodiment, the resultant extract of the defatting procedure can be further processed via acid hydrolysis to produce another type of plant extract that can be added to the nutritional composition of the present invention. The acid hydrolysis procedure can be conducted under any suitable process condition with any suitable types and amounts of solvents, including, for example, ethyl acetate.

In an embodiment, the extract from the defatting procedure can be further processed via a solvent extraction procedure. The solvent extraction can be carried out under any suitable process conditions and in the presence of any suitable amount and type of solvent. In an embodiment, the solvent includes a solution of methanol ("MeOH") and water mixed in a 1:1 volume ratio. The resultant solution of the solvent extraction procedure can be further processed by evaporation of the solvent under suitable conditions to produce another extract. Alternatively, the resultant solution can be treated with an adsorbant agent, such as polyvinylpolypyrrolidone or the like, to trap polyphenols. The adsorbant agent treatment can be carried out under any suitable process conditions.

The amount of chicoric acid and/or natural source thereof in the product will depend on several factors, such as the nature of the extract, the condition of the plant, the age, condition and size of the person or animal to be treated, the frequency, the product will be administered and/or the specific kind of skin disorder or damage to be treated or prevented or desired cosmetic effect.

The present inventors have found that the effectiveness of chicory or an extract thereof according to the present invention is generally dose dependant and follows a dose response curve. If generally mild skin disorders or damages are to be prevented and the product will be used frequently, very small amounts of chicory or an extract thereof will be sufficient to achieve the desired effect. If a severe skin pigment disorder is to be treated, larger amounts of chicory or an extract thereof will be more appropriate, although also small amounts will produce an effect.

Generally, it is preferred if the ingredient is enriched in chicoric acid and/or derivatives thereof. For example, the ingredient and/or the composition may comprise chicoric acid and/or derivatives thereof in an amount in the range of 0.001-99.99 weight-% of dry weight, preferably 0.1-50 weight-% of dry weight, most preferred 0.1-10 weight-% of dry weight. The ingredient and/or the composition may comprise the lactic acid bacterium capable of hydrolyzing chicoric acid and/or derivatives thereof to generate tartaric and/or caffeic acid in an amount in the range of 0.001-99.99 weight-% of dry weight, preferably 0, 1-50 weight-% of dry weight, most preferred 0.1-10 weight-% of dry weight.

Generally, it is preferred if the product contains chicory or an extract thereof in an amount in the range of about 0.1 g/l to 10 g/l, preferably in the range of 0.5 g/l to 3 g/l product. If the total amount of product cannot be measured in litres it is preferred if the product contains chicory or an extract thereof in an amount in the range of about 0.1 g/kg to 10 g/kg, preferably in the range of 0.5 g/kg to 3 g/kg product. Preferably the product contains chicory or an extract thereof in a daily dose of 0.01 g-100 g, preferably 0.25 g-10 g.

The compositions according to the invention may be in any of the galenical forms usually available for the method of administration selected.

Oral Compositions

The compositions according to the invention may be in any of the galenical forms normally available for the method of administration selected. The carrier may be of diverse nature depending on the type of composition under consideration.

In particular, the chicory or extract thereof may be incorporated into any form of food supplement, For example, it may be present in capsules, gelatin capsules, soft capsules, tablets, sugar-coated tablets, pills, pastes or pastilles, gums, or drinkable solutions or emulsions, a syrup or a gel. Such a supplement might also include a sweetener, a stabilizer, an antioxidant, an additive, a flavouring agent and/or a colorant. The formulation thereof is carried out by means of the usual methods for producing sugar-coated tablets, gel capsules, gels, hydrogels for controlled release, emulsions, tablets or capsules.

Use

The products of the invention may be efficiently used for treating or preventing skin pigmentation disorders or cosmetically lightening skin tone e.g. by decreasing the production of melanin. Indeed chicoric acid and chicory extracts were shown to decrease in vitro the synthesis of melanin (Example 1, FIG. 1). The production of tyrosinase was also decreased but to a limited extent (FIG. 2), suggesting that the decrease in melanin was not due to tyrosinase inhibition but rather to mechanisms acting upstream or downstream of this enzyme.

The ingredients according to the present invention have further a positive effect on strengthening skin barrier and maintaining skin hydration.

As a result, the pigment imperfections are reduced, the complexion becomes brighter and more homogeneous, without areas of dyschromia, or of dryness.

Thus, according to one subject, the invention relates to the cosmetic use of an effective amount of at least one ingredient containing chicoric acid and/or derivatives as an active agent for treating and/or preventing skin pigmentation disorders, in particular those due to age or environmental factors such as UV.

The present invention is also directed towards the cosmetic use of an effective amount of at least one ingredient containing chicoric acid and/or derivatives as an active agent for whitening or lightening skin tone, which is particularly desirable for asian population.

A use in accordance with the present invention may also comprises the use of at least one ingredient containing chicoric acid and/or derivatives, in combination with an effective amount of at least one active agent for improving skin hydration or skin ageing, in particular as described hereinafter.

According to another of its aspects, the subject of the invention is a method, in particular a cosmetic method, for treating and/or preventing skin tone imperfections and/or disorders associated with hyper-pigmentation, in particular aesthetic disorders, in an individual, comprising at least one step of administering, to said individual, at least one ingredient containing chicoric acid and/or derivatives according to the invention.

The cosmetic treatment method of the invention may be carried out in particular by orally administering at least an effective amount of at least one ingredient containing chicoric acid and/or derivatives in accordance with the invention. Oral administration comprises ingesting, in one or more intakes, an oral composition as defined above.

It may comprise a single application. According to another embodiment, the application is repeated, for example, 2 to 3 times a day, for one day or more, and generally for a sustained period of at least 4, or even 1 to 15, weeks.

In addition, combinations of treatment with, optionally, oral or topical forms may be envisaged in order to supplement or reinforce the activity of the ingredients as defined by the invention.

Thus, a topical or oral treatment with a composition containing Chicory or an extract thereof in accordance with the invention, combined with an oral or topical composition optionally containing another active ingredient, in particular a probiotic microorganism, or other probiotics in dead, live or semi-active form or an hydrating or anti-ageing agent could be imagined as a kit. The ingredients are mixed, before they are formulated, in the order and under conditions readily determined by those skilled in the art.

The ingredients are mixed, before they are formulated, in the order and under conditions readily determined by those skilled in the art.

Further advantages and features of the present invention are apparent from the following Examples and Figures. The examples hereinafter are thus presented by way of non-limiting illustration of the field of the invention. In these examples, unless otherwise indicated, the percentages are percentages by weight and the ranges of values written in the form "between . . . and . . . " include the upper and lower limits specified.

FIGURES

FIG. 1: Melanin production by murine melanocytes pre-treated with chicoric acid or chicory extract vs controls (positive/negative).

Figure 2:
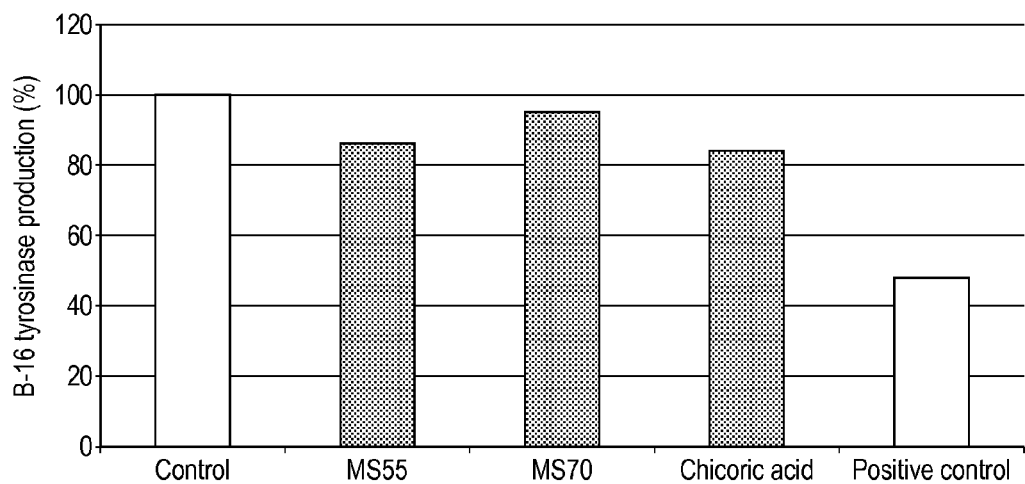

FIG. 2: tyrosinase production by murine melanocytes pre-treated with chicoric acid or chicory extract vs controls (positive/negative).

Figure 3:
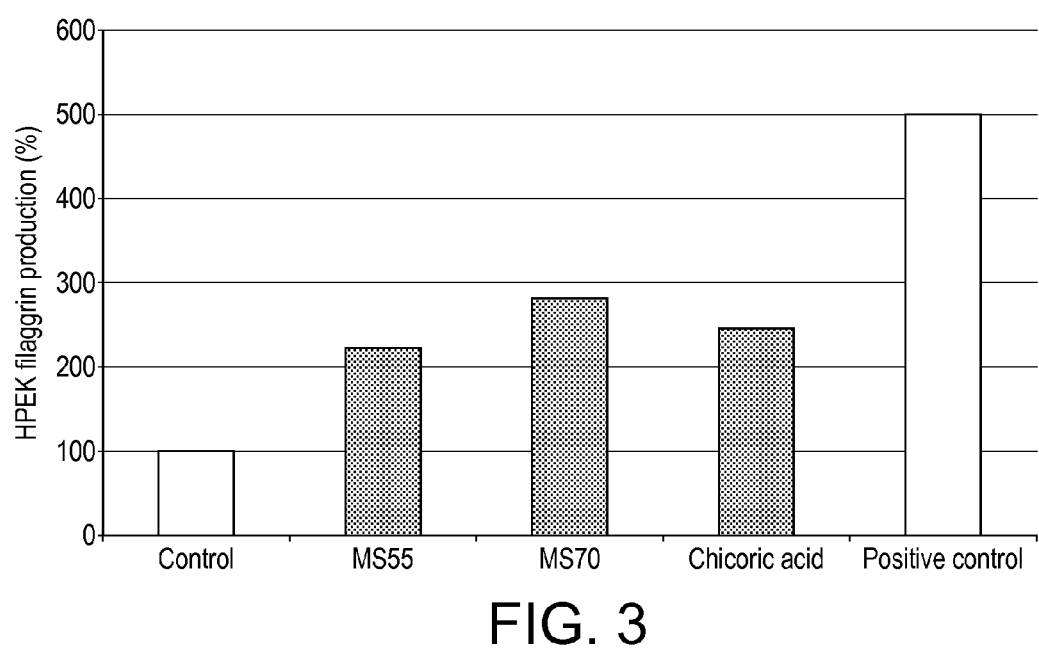

FIG. 3: Filaggrin synthesis by human primary epidermal keratinocytes pre-treated with chicoric acid or chicory extract vs controls (positive/negative).

EXAMPLES

Example 1

Effect of Chicoric Acid and Chicory Extract on Skin Pigmentation

In order to evaluate the potential beneficial effect of ingredients towards skin de- or pro-pigmentation we used 2D culture of murine melanocytes (B16) and we performed 2 tests: 1-assessment of melanin production and 2-assessment of tyrosinase production.

1. The Cell Culture Conditions.

B16 cells were cultured in DMEM 1 g/L glucose without phenol red supplemented with 10% foetal calf serum, in a humidified chamber at 37° C. and containing 5% $CO_2$.

2. The Production of Melanin by B16 Murine Melanocyte Cell Line.

Cells were incubated with the selected ingredients or the test references (Kojic acid at 400 µg/mL) for 72 hours, in the presence or absence of NDP-MSH an analog of MSH. The total quantity of melanin (extracellular and intracellular) was evaluated by measurement of the optical density at 405 nm of each sample against melanin standards in presence or in absence of NDP-MSH.

3. The Production of Tyrosinase by B16 Murine Melanocyte Cell Line.

Cells were incubated with the selected ingredients or the test references (Kojic acid at 400 µg/mL) for 48 hours. The production of tyrosinase was evaluated by immunolabeling.

Ingredients:

We have tested two chicory extracts MS-55 (concentré MS-55 LEROUX) and MS-70 (pâte MS-70 LEROUX) and Chicoric acid. The tested concentrations are showed in Table 1 below.

| Ingredient | Highest non cytotoxic conc. on HDF (mg/mL) | Highest non cytotoxic conc. on HPEK (mg/mL) | Tested conc. on HDF (mg/mL) | Tested conc. on HPEK (mg/mL) |
| --- | --- | --- | --- | --- |
| MS55 10 mg/ml in NaPO4 10 mM pH 7.0 | 10 | 10 | 0.4 | 10 |
| Chicoric acid 10 mM ie 4.74 mg/ml | 0.2 mM | 0.2 mM | 0.2 mM | 0.04 mM |
| MS70 10 mg/ml in NaPO4 10 mM pH 7.0 | 2 | 10 | 0.4 | 10 |

Results

Results are expressed in percentage relative to the control. Test reference (Kojic acid) induced, as expected a decrease in melanin production. FIG. 1 shows the melanin production by B16 melanocytes treated for 72 hours with the selected ingredients.

Chicory extract MS-55 was shown to decrease in vitro the production of melanin by 60% (FIG. 1) whereas chicoric acid decreased melanin production by 90%. The production of tyrosinase was also decreased by these ingredients but to a limited extent (less than 20% for both MS-55 and chicoric acid, FIG. 2), suggesting that the decrease in melanin was not due to tyrosinase inhibition but rather to mechanisms acting upstream or downstream of this enzyme.

Example 2

Effect of Chicoric Acid and Chicory Extract on Skin Barrier Function and Skin Hydration The potential beneficial effect of the Extracts of Example 1 towards skin barrier function and skin hydration was evaluated by using 2D culture of human primary epidermal keratinocytes and we assessed the synthesis of filaggrin The Cell Culture Conditions.

Human epidermal keratinocytes were cultured in control keratinocytes-SFM medium, in a humidified chamber at 37° C. and containing 5% CO2.

The Synthesis of Filaggrin by Human Epidermal Keratinocytes.

Cells were incubated with the selected ingredients or the test references (CaCl2 at 1.5 mM) for 144 hours. The production of filaggrin by was evaluated by immunolabeling.

Results

The results are showed in FIG. 3. Pre-treatment of the cells with chicory extracts MS-55, MS-70 and chicoric acid resulted in an increase of filaggrin suggesting that these extracts could strengthen skin barrier (FIG. 3). A stronger skin barrier ensures a better protection of the body from the environment and pathogens' attack. It also limits the loss of water through the epidermis, thus ensuring an appropriate skin hydration.

Example 3

Powder Stick

| Ingredients | Amount |
|---|---|
| Active ingredient | |
| chicory extract MS-55 | 8 g |
| Excipient | |
| Maltodextrin | qs 30 g |
| Xanthan gum | 0.8 mg |
| Sodium benzoate | 0.2 mg |

One stick can be taken per day.

The invention claimed is:

1. A method for treating an individual having a skin pigment disorder and/or skin pigment imperfection associated with hyperpigmentation, comprising a step of administering orally to said individual a food supplement which contains a daily dose of 0.01 g to 100 g of Chicory extract; wherein said Chicory extract comprises chicoric acid and/or derivatives in an effective amount in the range of 0.001-99.99 weight % of dry weight of the Chicory extract.

2. Method in accordance with claim 1, wherein the skin disorder is selected from the group consisting of melasma, freckles, and age spots.

3. Method in accordance with claim 1 for improving skin tone and/or skin complexion.

4. A method for lightening and/or whitening skin tone in an individual in need thereof, comprising a step of administering orally to said individual a food supplement which contains a daily dose of 0.01 g to 100 g of Chicory extract; wherein said Chicory extract comprises chicoric acid and/or derivatives in an effective amount in the range of 0.001-99.99 weight % of dry weight of the Chicory extract.

5. Method in accordance with claim 1, wherein the Chicory extract is obtained by extraction with a solvent from Chicory plant material.

6. Method in accordance with claim 1, wherein the said Chicory extract is administered in a daily dose of 0.25 g-10 g.

7. Method in accordance with claim 1, wherein the said Chicory extract comprises chicoric acid and/or derivatives in an amount of 0.1 to 99.99 weight % of dry weight.

8. Method in accordance with claim 1, wherein the food supplement comprises at least one kind of food grade micro-organisms.

9. Method in accordance with claim 1, wherein the food supplement includes an effective amount of at least one active agent for improving skin hydration or skin ageing.

10. Method in accordance with claim 4, wherein the Chicory extract is obtained by extraction with a solvent from Chicory plant material.

11. Method in accordance with claim 4, wherein the Chicory extract is administered in a daily dose of 0.25 g-10 g.

12. Method in accordance with claim 4, wherein the said Chicory extract comprises chicoric acid and/or derivatives in an amount in the range of 0.1 to 10 weight % of dry weight.

13. Method according to claim 1, wherein the oral administration of said food supplement is repeated 2 to 3 times a day, for at least 4 weeks.

14. Method according to claim 4, wherein the oral administration of said food supplement is repeated 2 to 3 times a day, for at least 4 weeks.

15. Method in accordance with claim 1, wherein said Chicory extract is obtained after a defatting procedure on a plant material, to produce an extract that results from fats removed from the plant material.

16. Method in accordance with claim 4, wherein said Chicory extract is obtained after a defatting step on a plant material, to produce an extract that results from fats removed from the plant material.

17. Method in accordance with claim 1, wherein the food supplement is selected from a group consisting of: capsules, gelatin capsules, soft capsules, tablets, sugar-coated tablets, pills, pastes, pastilles, gums, drinkable solutions, emulsions, syrups and gels.

18. Method in accordance with claim 4, wherein the food supplement is selected from a group consisting of: capsules, gelatin capsules, soft capsules, tablets, sugar-coated tablets, pills, pastes, pastilles, gums, drinkable solution, emulsions, syrups and gels.

19. Method in accordance with claim 1, wherein the food supplement is enriched in chicoric acid and/or derivatives thereof.

20. Method in accordance with claim 4, wherein the food supplement is enriched in chicoric acid and/or derivatives thereof.

* * * * *